United States Patent [19]

Kuppinger, deceased et al.

[11] 4,177,526
[45] Dec. 11, 1979

[54] SECURING DEVICE FOR AN INTRAOCULAR LENS

[76] Inventors: John C. Kuppinger, deceased, late of Harlingen, Tex., by Charlotte W. Kuppinger, executrix, 1515 N. Ed Carey Dr., Harlingen, Tex. 78550

[21] Appl. No.: 818,003

[22] Filed: Jul. 22, 1977

[51] Int. Cl.² ............................ A61F 1/16; A61F 1/24
[52] U.S. Cl. .................................................... 3/13
[58] Field of Search .................................... 3/13, 1

[56] References Cited
U.S. PATENT DOCUMENTS

| | | | |
|---|---|---|---|
| 3,913,148 | 10/1975 | Potthast | 3/13 |
| 4,073,014 | 2/1978 | Poler | 3/13 |

Primary Examiner—Ronald L. Frinks
Attorney, Agent, or Firm—Lowe, Kokjer, Kircher, Wharton & Bowman

[57] ABSTRACT

An artificial lens is adapted to be implanted within the eye to replace the natural lens. A pair of arms projecting from the lens are held by a frangible thread such that the tips of the arms are spaced from but biased toward the peripheral portion of the lens. The lens is implanted immediately in front of the iris with the arms inserted behind the iris. After implanting of the lens, a laser beam is employed to break the thread. The arms then spring forwardly in a manner to firmly pinch the iris between their tips and the peripheral region of the lens.

4 Claims, 3 Drawing Figures

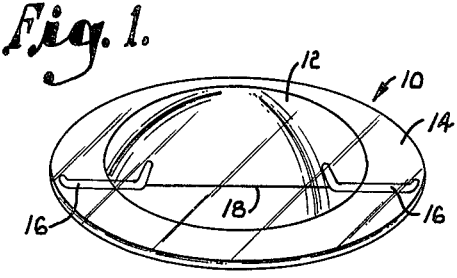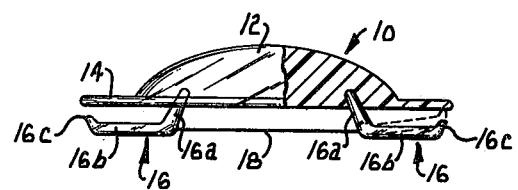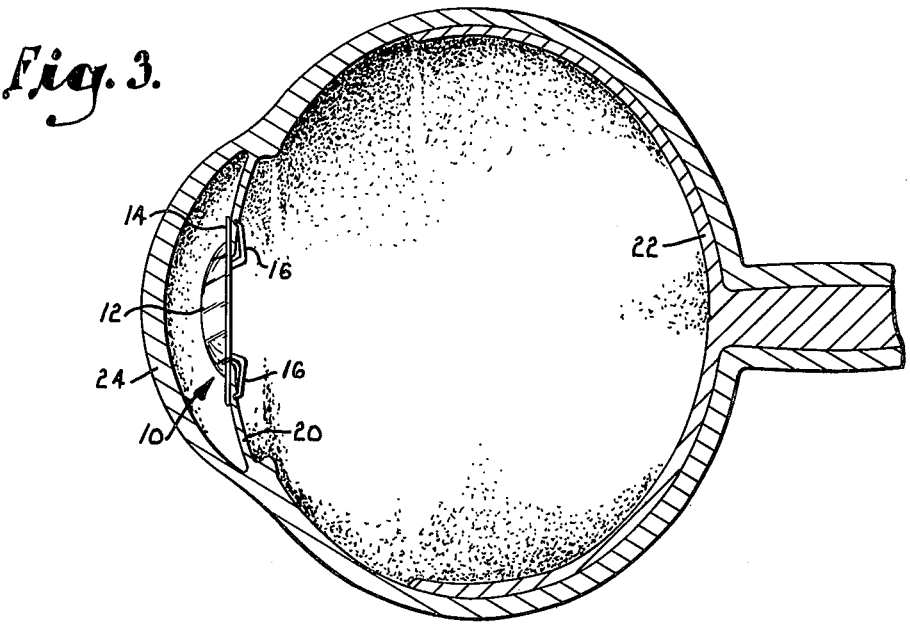

SECURING DEVICE FOR AN INTRAOCULAR LENS

BACKGROUND AND SUMMARY OF THE INVENTION

This invention relates generally to intraocular lenses and deals more specifically with an improved arrangement and method for securing such lenses within the eye.

Following removal of the natural lens during cataract surgery, an artificial intraocular lens is often implanted in the eye. In order to prevent adverse effects such as distortion of the vision, it is necessary for the implanted lens to be securely retained in the correct position in the pupillary region. However, due to the drawbacks of the lens securing devices that have been proposed in the past, it is not unusual for the lens to become dislocated, thereby causing discomfort, visual distortion, and other harmful effects.

At present, the lens is normally implanted immediately in front of the iris and is typically provided with projecting bars or loops which are placed loosely behind the iris. Since the bars and loops fit loosely behind the iris, they are able to pass forwardly through the pupillary aperture when dilation occurs. Consequently, the lens becomes completely disconnected from the iris and is able to assume an improper position in the eye. Although eye drops have been used to combat this problem by controlling dilation of the iris, such a solution is inconvenient at best.

It has also been proposed to fix the lens to the iris by means of a suture or a metal clip or hook, either alone or together with loops and bars such as those described previously. Aside from the additional time and difficulty involved in performing the surgery, this proposal has not successfully eliminated the problem of dislocation of the lens. For practical reasons, the suture or clip is ordinarily applied only to one side of the lens so that the opposite side is still able to become improperly oriented with respect to the iris, particularly when the pupil becomes dilated.

It is the primary object of the present invention to provide an improved intraocular lens structure which may be firmly secured in the pupillary region of the eye.

Another object of the invention is to provide an intraocular lens structure which may be easily implanted and thereafter secured in the appropriate position during the postoperative period. Significantly, the lens need not be secured at the time of surgery but can instead be fixed in place at a later time after the surgeon has had an opportunity to confirm that the lens is positioned correctly.

A further object of the invention is to provide a lens of the character described which includes a pair of arms that coact with the lens to pinch the iris in a manner preventing dislocation of the lens, even during dilation.

Still another object of the invention is to provide a lens of the character described which is economical to manufacture and easy to implant and secure within the eye.

A further object of the invention is to provide a method of placing and securing an intraocular lens in the eye.

Other and further objects of the invention, together with the features of novelty appurtenant thereto, will appear in the course of the following description.

DETAILED DESCRIPTION OF THE INVENTION

In the accompanying drawing which forms a part of the specification and is to be read in conjunction therewith and in which like reference numerals are used to indicate like parts in the various views:

FIG. 1 is a perspective view of an intraocular lens constructed in accordance with a preferred embodiment of the present invention.

FIG. 2 is an end view of the lens shown in FIG. 1, with a portion broken away for illustrative purposes and the broken lines indicating movement of one of the arms to the securing position against the lens; and FIG. 3 is a top plan view taken in section through the eye and showing the lens secured to the iris.

Referring to the drawing in detail, numeral 10 generally designates an artificial intraocular lens. The lens 10 may be made of any suitable transparent substance such as a synthetic material of the type commonly used to form such lenses, for example, methyl methacrylate. The lens has the usual thickened convex central portion 12 which is surrounded by a flat annular peripheral portion 14. The shape and construction of the lens is conventional.

In accordance with the invention, the lens 10 is provided with a pair of arms 16 which serve to secure the lens in place within the eye. Each arm is a generally L-shaped member having a relatively short stub portion 16a that connects with the side of the lens opposite the thickened convex portion 12. To accomplish this connection, holes are drilled in the lens at locations offset on opposite sides of its center, and the stubs are press fit into these holes. Preferably, the stubs taper toward their ends.

Connected with the stub portion 16a of each arm is a straight portion 16b which extends outwardly in a generally radial direction at a location spaced behind the lens. Each portion 16b has a small tapered tip 16c which is turned generally toward the lens to assist in gripping the iris, as will become clear. The connection of each arm 16 to the lens is made in a manner to bias the arms in a direction urging the tips 16c against the lens at diametrically opposite locations near its periphery. In the preferred embodiment, arms 16 are made of a synthetic substance such as nylon, although they may be any suitable material having the required resiliency.

Arms 16 are initially interconnected by a frangible thread 18 which extends between the outer ends of the stub portions 16a in a tensed condition. The thread 18 may be a thin strand of nylon or another substance capable of holding the arms displaced from their normal position. In the displaced position, which is best shown in FIG. 2, tips 16c are spaced well behind the peripheral lens portion 14. Thread 18 is preferably dark colored so that it will be able to absorb heat from a laser beam which is employed to break the thread, as will be explained more fully.

After removal of the natural lens (not shown), lens 10 is implanted in the eye by standard surgical techniques. The lens is implanted in the pupillary region with its peripheral portion 14 located immediately in front of the iris, which is indicated by numeral 20 in FIG. 3. Since tips 16c are spaced from the lens, arms 16 may be easily placed behind the iris during the surgery. The convex lens portion 12 substantially spans the pupillary aperture.

After completion of the implanting, the surgeon can confirm in the postoperative period that the lens is positioned correctly. If so, thread 18 is broken by a laser beam in order to secure the lens firmly in place within the eye. The laser beam is directed into the eye at a rather sharp angle in order to avoid being focused on the central area of the retina 22. The laser beam readily passes through the transparent cornea 24 and the lens 10, as well as any fluid that is encountered. However, the opaque thread 18 absorbs the intense energy of the beam and breaks, thus allowing the arms 16 to assume their normal positions. Consequently, tips 16c spring forwardly toward the lens such that the iris 20 is firmly pinched between the lens and each of the tips 16a. The lens is maintained in the correct position, even during dilation, due to the continuous pinching action of the arms against the iris. Although a firm pinching action is adequate in most cases, it is contemplated that in some situations the tapered tips 16c will impale the iris in order to provide a particularly secure attachment of the lens.

Although the lens 10 is illustrated as being implanted forwardly of the iris and the arms 16 behind it, it is to be understood that in some cases an opposite arrangement may be desirable. Thus the lens may be behind the iris with the arms in front of it. Such modification is apparent to those skilled in the art and is within the scope of the invention.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawing is to be interpreted as illustrative and not in a limiting sense.

Having thus described the invention, I claim:
1. An intraocular lens structure comprising:
a lens adapted to be implanted in the pupillary region of the eye adjacent the iris;
a plurality of resilient L-shaped arms on one face of the lens with one end of one leg of each arm anchored in the lens and the other leg extending outwardly toward the periphery of the lens and terminating in a free end; and
a frangible tension member connecting said arms and of a length such that the arms are held in a position such that the free ends are spaced away from the confronting surface of the lens, said frangible member constructed in a manner to be capable of being severed by a laser beam whereby to release the arms to effect pinching of the iris between the lens surface and said free ends.

2. The method of placing and securing an intraocular lens in the eye with the rim of the lens adjacent the iris, said method comprising the steps of
positioning a plurality of resilient L-shaped arms on the face of the lens with one end of one leg of each arm anchored in the lens and the other leg extending outwardly toward the periphery of the lens and terminating in a free end,
interconnecting said arms with a frangible tension member, the interconnection being such that the free ends of said other legs are resiliently spaced away from the lens surface,
positioning the lens in the pupillary region of the eye with portions of the iris located in the spaces between said free ends of said arms and the lens surface, and
severing said tension member thereby to cause said arms to clamp the adjoining portions of said iris between said lens surface and said free ends.

3. A method as in claim 2 wherein said severing is effected by impacting said tension member with a laser beam.

4. The method as in claim 2 wherein said lens is located with the lens principally on the exterior of the iris and the arms within the iris.